(12) United States Patent
Gregersen et al.

(10) Patent No.: US 10,328,048 B2
(45) Date of Patent: Jun. 25, 2019

(54) CAFESTOL FOR TREATING DIABETES

(71) Applicants: Aarhus Universitet, Aarhus C (DK); Region Midtjylland, Viborg (DK)

(72) Inventors: Søren Gregersen, Egå (DK); Per Bendix Jeppesen, Egå (DK); Kjeld Hermansen, Egå (DK); Fredrik Brustad Mellbye, Aarhus C (DK)

(73) Assignees: Aarhus Universitet, Aarhus C (DK); Region Midtjylland, Viborg (DK)

( * ) Notice: Subject to any disclaimer, the term of this patent is extended or adjusted under 35 U.S.C. 154(b) by 0 days.

(21) Appl. No.: 15/314,740

(22) PCT Filed: Jun. 1, 2015

(86) PCT No.: PCT/DK2015/050139
§ 371 (c)(1),
(2) Date: Nov. 29, 2016

(87) PCT Pub. No.: WO2015/180736
PCT Pub. Date: Dec. 3, 2015

(65) Prior Publication Data
US 2017/0231946 A1 Aug. 17, 2017

(30) Foreign Application Priority Data
May 30, 2014 (DK) .................. 2014 70314

(51) Int. Cl.
*A61K 31/343* (2006.01)
*A61K 45/06* (2006.01)

(52) U.S. Cl.
CPC ............ *A61K 31/343* (2013.01); *A61K 45/06* (2013.01)

(58) Field of Classification Search
CPC .................................................. A61K 31/343
See application file for complete search history.

(56) References Cited

U.S. PATENT DOCUMENTS

| 4,793,990 A | 12/1988 | Grollier et al. |
| 8,226,992 B1 * | 7/2012 | Okerlin, III ........... A61K 36/74 424/725 |
| 2009/0175973 A1 | 7/2009 | Vikhrieva |
| 2009/0181933 A1 | 7/2009 | Bingaman et al. |

FOREIGN PATENT DOCUMENTS

| FR | 2855057 | | 11/2004 |
| JP | 2011-032217 | * | 2/2011 |
| JP | 201132217 A | | 2/2011 |
| WO | WO-1998/10739 | | 3/1998 |
| WO | WO-2004/073607 | | 9/2004 |
| WO | WO-2007/025275 | | 3/2007 |

OTHER PUBLICATIONS

Van Dieren et al. Diabetologia, 2009, vol. 52, pp. 2561-2569.*
JP 2011-032217 English Translation (13 pages) (Machine Translated on Sep. 11, 2017).*
Gorter et al. Clinical Evidence, 2012; 10:609 (pp. 1-106.*
Berge, S. et al., Pharmaceutical Salts; Journal of Pharmaceutical Sciences, 66(1): 1-19, 1977.
De Roos et al., Absorption and urinary excretion of the coffee diterpenes cafestol and kahweol in healthy ileostomy volunteers, Journal of Internal Medicine, 244: 451-460, 1998.
Ding, M. et al., Caffeinated and Decaffeinated Coffee Consumption and Risk of Type 2 Diabetes: A Systematic Review and a Dose-Response Meta-Analysis, Diabetes Care, 37(2): 569-86, Feb. 2014.
Hermansen, Kjeld et al., Kaffe, Sundhed og Sygdom / Coffee, Health and Disease, May 26, 2012, vol. 1, Vidensråd for Forebyggelse / Danish Council on Health and Disease Prevention, Denmark, Copenhagen.
Concise explanation of the relevance of Hermansen, Kjeld et al., Kaffe, Sundhed og Sygdom / Coffee, Health and Disease, May 26, 2012, vol. 1, Vidensråd for Forebyggelse / Danish Council on Health and Disease Prevention, Denmark, Copenhagen.
Higdon J. et al., Coffee and Health; A Review of Recent Human Research, Critical Reviews in Food Science and Nutrition; 46:101-123; 2006.
Lam, L. et al., Effects of Derivatives of Kahweol and Cafestol on the Activity of Glutathione S-Transferase in Mice, Journal of Medicinal Chemistry, 30(8): 1399-1403, 1987.
Merlotti, C. et al., Prevention of type 2 diabetes; a systematic review and meta-analysis of different intervention strategies, 16(8): 719-727, Aug. 2014.
Miller, E. et al., Kahewol and Cafestol: Inhibitors of Hamster Buccal Pouch Carcinogenesis, Nutrition and Cancer, 15(1): 41-46 1991.
Ranheim, T. et al., Coffee Consumption and human health—beneficial or detrimental?—Mechanisms for effects of coffee consumption on different risk factors for cardiovascular disease tand type 2 diabetes mellitus, Molecular Nutrition & Food Research, 49(3) 274-284, 2005.
Urgert, R.et al., Effects of cafestol and kahweol from coffee grounds on serum lipids and liver enzymes in humans, The American Journal of Clinical Nutrition, 61(1): 149-155, Jan. 1995.
Kempf, K. et al., Effects of coffee consumption on subclinical inflammation and other risk factors for type 2 diabetes: a clinical trial, American Journal of Clinical Nutrition, 91(4): 950-957, Feb. 24, 2010.
Kim, H. et al., The coffee diterpene kahweol inhibits tumor necrosis factor-alpha-induced expression of cell adhesion molecules in human endothelial cell, Toxicology and Applied Pharmacology, 217:332-341, Oct. 4, 2006.

(Continued)

*Primary Examiner* — James D. Anderson
(74) *Attorney, Agent, or Firm* — Julie K. Staple; Dinsmore & Shohl LLP

(57) ABSTRACT

A method is provided of treating, preventing or ameliorating type 2 diabetes and/or a clinical condition associated with type 2 diabetes, which method comprises administering an effective amount of cafestol or a derivative thereof including esters and salts thereof to a person in need thereof. Further provided are compositions comprising cafestol and at least one additional agent suitable for treating, preventing or ameliorating diabetes and/or a clinical condition associated with diabetes. A method is also provided of increasing insulin secretion and/or increasing insulin-dependent glucose uptake, said method comprising administering an effective amount of cafestol or a derivative thereof to a person in need thereof.

9 Claims, 6 Drawing Sheets

(56) References Cited

OTHER PUBLICATIONS

Ludwig. I. et al., Coffee: biochemistry and potential impact on health: Food & Function, 5(8): 1695-1717, Mar. 20, 2014.

Porez, G. et al., Bile acid receptors as targets for the treatment of dyslipidemia and cardiovascular disease: Thematic Review Series: New Lipid and Lipoprotein Targets for the Treatment of Cardiometabolic Diseases; The Journal of Lipid Research, 53: 1723-1737, May 1, 2012.

Ricketts, M. et al., The Cholesterol-Raising Factor from Coffee Beans, Cafestol, as an Agonist Ligand for the Farnesoid and Pregnane X Receptors, Molecular Endocrinology, 21(7): 1603-1616, Apr. 24, 2007.

Lopez-Garcia, E. et al., Coffee consumption and markers of inflammation and endothelial dysfunction in healthy and diabetic women, Am J Clin Nutr, 8:888-93, 2006.

Lopez-Garcia, E.; Coffee consumption and risk of chronic diseases: changing our views, Am J Clin Nutr, 95: 787-788, Mar. 7, 2012.

Natella, F. et al., Role of coffee in modulation of diabetes risk, Nutrition Reviews, 70(4):207-217, 2012.

Salazar-Martinez et al., Coffee Consumption and Risk for Type 2 Diabetes Mellitus, Annals of Internal Medicine, 140:1-8, Jan. 6, 2004.

Sridevi, V. et al., Evaluation of Roasting and brewing effect on Antinutritional Diterpenes-Cafestol and Kahweon in Coffee, Global Journal of Medical Research, 11(5), Dec. 2011.

Zhang, C. et al., Cafestol extraction yield from different coffee brew mechanisms, Food Research International, 49: 27-31, 2012.

\* cited by examiner

Acute insulin secretion studies (INS1-E) with Cafestol

Chronic Insulin secretion studies (INS1-E) with cafestol

CAFESTOL FOR TREATING DIABETES

FIELD OF INVENTION

The present invention relates to the use of cafestol compounds in the treatment of diabetes and/or a clinical condition associated with diabetes.

BACKGROUND OF INVENTION

Coffee consumption has been associated with reduced risk of type 2type 2 diabetes; cf. Merlotti C, Morabito A, Pontiroli A E.: Prevention of type 2 diabetes; a systematic review and meta-analysis of different intervention strategies; Diabetes, obesity and metabolism. 2014 Jan. 29; Ding M, Bhupathiraju S N, Chen M, van Dam R M, Hu F B.: Caffeinated and Decaffeinated Coffee Consumption and Risk of Type 2 Diabetes: A Systematic Review and a Dose-Response Meta-analysis; Diabetes Care. 2014 February; 37(2):569-86. doi: 10.2337/dc13-1203; Higdon J V, Frei B.: Coffee and health: a review of recent human research; Crit Rev Food Sci Nutr. 2006; 46(2):101-23. US 2009/0175973 proposes the use of coffee cherry and isolates thereof for treating diabetes.

Cafestol is a diterpenoid found in coffee, and diverse biological activities have been attributed to cafestol and related compounds. For example, coffee bean oil, which contains cafestol and kahweol, has been claimed to be useful as a sun filter (U.S. Pat. No. 4,793,990). An extract of essential oils of coffee has been used, in combination with numerous other components, including cocoa butter and antioxidants, in toilet soap compositions; the components are said to synergistically interact to provide a "monomolecular film" on the skin (SU 1770352). Further, cafestol itself, in combination with kahweol, has been suggested as having a protective effect against carcinogens in animals (Miller et al., Nutr. Cancer 15: 41-46, 1991; Huggett and Schilter, Colloq. Sci. Int. Cafe[C.R.] 16(1): 65-72, 1995). Cafestol and kahweol have also been linked to increasing serum lipid concentrations in individuals consuming significant quantities of unfiltered coffee (Urgert et al., Am. J. Clin. Nutr. 61: 149-154, 1995).

SUMMARY OF INVENTION

A main object of the present invention is to provide methods of treating diabetes and related disorders by use of cafestol compounds, as cafestol affects the secretion of insulin by insulin-producing cells and also increases insulin sensitivity.

In one aspect, the invention relates to a method of treating, preventing or ameliorating diabetes and/or a clinical condition associated with diabetes, which method comprises administering an effective amount of cafestol or a derivative thereof including esters and salts thereof to a person in need thereof. The clinical condition is preferably insulin resistance, and/or type 2 diabetes. The cafestol compound may also be combined with an additional agent such as a member of the group consisting of biguanides (metformin), sulfonylureas, meglitinides (glinides), acarbose, bile acid sequestrants, dopamine-2-agonists, amylin mimetics, thiazolidinediones (glitazones), glucagon-like peptide-1 receptor agonists, dipeptidyl peptidase 4 inhibitors (DPP4 inhibitors), sodium-glucose co-transporter 2 (SGLT2) inhibitors, G protein-coupled receptor agonists (e.g. GPR40 agonists), glucagon receptor antagonists, bromocriptine mesylate and insulins. Associated clinical conditions are for example selected from the group consisting of atherosclerosis, arteriosclerosis, arteriolosclerosis, hypertension, cardiovascular disorders, type 2 diabetes mellitus, retinopathy, neuropathy, nephropathy, microangiopathy, macroangiopathy, hyperglycemia, hypercholesterolemia, hyperinsulinemia, hyperlipidemia, overweight, visceral obesity, dyslipidemia, insulin resistance, impaired oral glucose tolerance, impaired fasting glucose, metabolic syndrome, polycystic ovary syndrome, fatty liver (steatosis hepatis), ischemia, ischemic heart disease, thrombotic stroke, haemorrhagic stroke, limb ischemia and/or claudication.

In a second aspect, a cafestol compound or a derivative thereof is provided for use in treating, preventing or ameliorating diabetes and/or a clinical condition associated with diabetes, in particular type 2 diabetes. Such use may also involve the combined use of cafestol compound and at least one additional agent suitable for treating, preventing or ameliorating diabetes and/or a clinical condition associated with diabetes; for example a member of the group consisting of biguanides (metformin), sulfonylureas, meglitinides (glinides), acarbose, bile acid sequestrants, dopamine-2-agonists, amylin mimetics, thiazolidinediones (glitazones), glucagon-like peptide-1 receptor agonists, dipeptidyl peptidase 4 inhibitors (DPP4 inhibitors), sodium-glucose co-transporter 2 (SGLT2) inhibitors, G protein-coupled receptor agonists (e.g. GPR40 agonists), glucagon receptor antagonists, bromocriptine mesylate and insulins.

The cafestol or a derivative thereof may be formulated as a pharmaceutical composition, i.e. a composition comprising a medical drug, or a food supplement.

In a third aspect, a composition is provided, which comprise cafestol or a derivative thereof and at least one additional agent suitable for treating, preventing or ameliorating diabetes and/or a clinical condition associated with diabetes.

A fourth aspect relates to a method of increasing insulin secretion and/or increasing insulin-dependent glucose uptake, said method comprising administering an effective amount of cafestol or a derivative thereof to a person in need thereof.

In a fifth aspect, a kit-of-parts is provided comprising a combined preparation containing cafestol or a derivative thereof and an additional agent suitable for treating, preventing or ameliorating diabetes and/or a clinical condition associated with diabetes, for the simultaneous, separate or sequential administration for treating, preventing or ameliorating diabetes and/or a clinical condition associated with diabetes. The additional agent may be selected from a member of the group consisting of biguanides (metformin), sulfonylureas, meglitinides (glinides), acarbose, bile acid sequestrants, dopamine-2-agonists, amylin mimetics, thiazolidinediones (glitazones), glucagon-like peptide-1 receptor agonists, dipeptidyl peptidase 4 inhibitors (DPP4 inhibitors), sodium-glucose co-transporter 2 (SGLT2) inhibitors, G protein-coupled receptor agonists (e.g. GPR40 agonists), glucagon receptor antagonists, bromocriptine mesylate and insulins.

The invention also in one aspect relates to a use of a cafestol compound or a derivative thereof for the manufacture of a medicament for treating, preventing or ameliorating diabetes and/or a clinical condition associated with diabetes, in particular type 2 diabetes.

In another aspect, a pharmaceutical composition is provided for treating, preventing or ameliorating diabetes and/or a clinical condition associated with diabetes, said composition comprising a cafestol compound or a derivative thereof.

DETAILED DESCRIPTION OF THE INVENTION

Terms and Definitions

Figure 1:
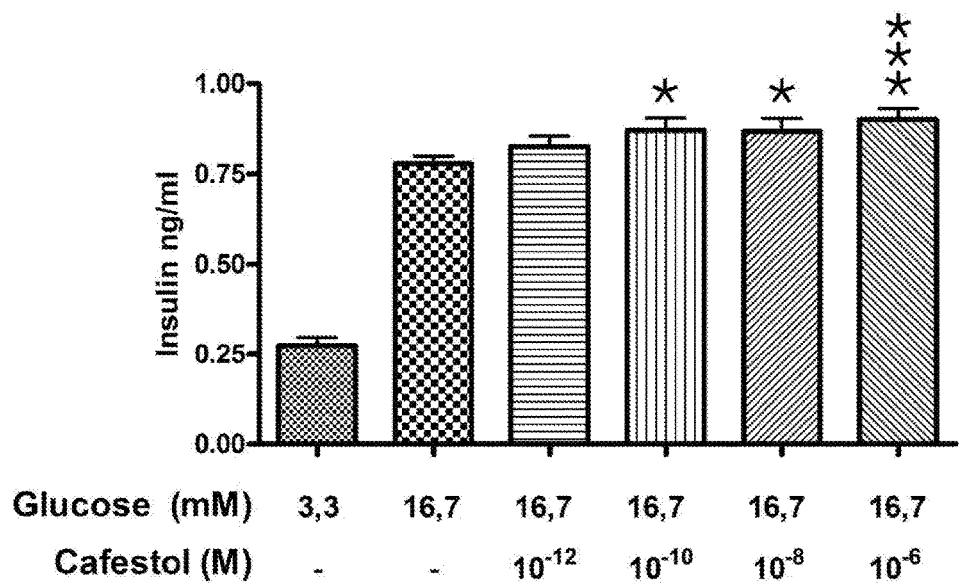
FIG. 1. Insulin secretion from INS-1E cells in response to cafestol.

To facilitate the understanding of the following description, a number of definitions are presented in the following paragraphs.

The term "treatment", as used anywhere herein comprises any type of therapy, which aims at terminating, preventing, ameliorating and/or reducing the susceptibility to a clinical condition as described herein. In a preferred embodiment, the term treatment relates to prophylactic treatment (i.e. a therapy to reduce the susceptibility of a clinical condition, a disorder or condition as defined herein).

Thus, "treatment," "treating," and the like, as used herein, refer to obtaining a desired pharmacologic and/or physiologic effect, covering any treatment of a pathological and/or clinical condition or disorder in a mammal, including a human. The effect may be prophylactic in terms of completely or partially preventing a disorder or symptom thereof and/or may be therapeutic in terms of a partial or complete cure for a disorder and/or adverse affect attributable to the disorder. That is, "treatment" includes (1) preventing the disorder or clinical condition from occurring or recurring in a subject, (2) inhibiting the disorder or clinical condition, such as arresting its development, (3) stopping or terminating the disorder or clinical condition or at least symptoms associated therewith, so that the host no longer suffers from the disorder or clinical condition or its symptoms, such as causing regression of the disorder or clinical condition or its symptoms, for example, by restoring or repairing a lost, missing or defective function, or stimulating an inefficient process, or (4) relieving, alleviating, or ameliorating the disorder or clinical condition, or symptoms associated therewith, where ameliorating is used in a broad sense to refer to at least a reduction in the magnitude of a parameter, such as inflammation, pain, and/or immune deficiency.

The terms "prevent", "preventing," and "prevention", as used herein, refer to a decrease in the occurrence of symptoms or characteristics of a disorder or clinical condition. The prevention may be complete. The prevention may also be partial, such that for example the occurrence of symptoms or characteristics of a disorder in a subject is less than that which would have occurred without the present invention. Prevention also refers to reduced susceptibility to a clinical condition.

The terms "ameliorate", "ameliorating" and "amelioration", are also used separately herein to refer to a reduction of the severity of the occurrence of symptoms or characteristics of a disorder or clinical condition.

The term "insulin resistance" as used herein, relates to a condition in which the cells no longer respond well to insulin. As a result, pancreatic cells will normally increase their insulin production and secrete more insulin into the bloodstream in an effort to reduce blood glucose levels and compensate for the insulin resistance. It is often linked to obesity, hypertension and high levels of fat in the blood. Many people with type 2 diabetes have insulin resistance.

The term "cardiovascular disorders" as used herein refer to the class of diseases that involve the heart and/or blood vessels (arteries and veins). Therefore, the term "cardiovascular disorder" refers to any disease that affects the cardiovascular system. Particularly, cardiovascular disorders comprise atherosclerosis, arteriosclerosis, and arteriolosclerosis. Cardiovascular disorders can be associated with diabetes, and thus, in one embodiment of the present invention, a disorder or clinical condition associated with diabetes is a cardiovascular disorder selected from the group consisting of atherosclerosis, arteriosclerosis, and arteriolosclerosis. However, atherosclerosis, arteriosclerosis, and arteriolosclerosis are also separate embodiments of the present invention, and can accordingly be claimed individually.

Atherosclerosis, a disease of the arteries, is one of the leading causes of death in the United States and Western Europe. The pathology of atherosclerosis and occlusive heart disease has been studied intensely, and a number of clinical conditions are therefore known to be associated with atherosclerosis. The earliest stage of atherosclerosis is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is presumed that most of the cholesterol found within the fatty streaks, in turn, gives rise to development of the "fibrous plaque", which consists of accumulated intimal smooth muscle cells loaded with lipid and surrounded by extra-cellular lipid, collagen, elastin and proteoglycans. The cells and the matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the lesion, which accounts for the arterial occlusion and tendency toward mural thrombosis and arterial muscle spasm that characterize advanced atherosclerosis. The term "atherosclerosis" as used herein, relates to the disease of the arteries, which is characterized by formation of fibrous plaques that become calcified and necrotic, advancing to a lesion, which may account for arterial occlusion and tendency toward mural thrombosis and arterial muscle spasm that characterize advanced atherosclerosis. It is understood, that the term "atherosclerosis" as used herein, relates to all the stages of development of that disease and any clinical condition associated therewith. Atherosclerosis may result in ischemic heart disease, thrombotic stroke, haemorrhagic stroke, as well as limb ischemia and claudication. The term "ischemic heart disease" as used herein, relates to any condition in which heart muscle is damaged or works inefficiently because of an absence or relative deficiency of its blood supply. Ischemic heart disease includes angina pectoris, acute myocardial infarction and chronic ischemic heart disease.

The term "thrombotic stroke" as used herein, relates to the disease state in which plaque formation inside a blood vessel blocks the flow of blood through the circulatory system. The term "haemorrhagic stroke" as used herein, relates to the disease state characterized by rupture of a vessel, which leads to internal bleeding, i.e. escape of blood to the extravascular space. In it understood that that term "haemorrhagic" as used herein, is meant to comprise all classes of haemorrhages.

The terms "limb ischemia" as used herein, relates to a restriction in the blood supply to the limbs, generally due to factors in the blood vessels, with resultant damage or dysfunction of tissue. Ischemia may result from a number of factors, including atherosclerosis. The term "claudication" as used herein, is related to limb ischemia and relates to a disease state with pain in the legs. Claudication usually occurs as a result of atherosclerosis.

Hypertension (or high blood pressure) is a condition, which occurs in the human population secondary to various other disorders such as renal artery stenosis, pheochromocytoma, or endocrine disorders. Hypertension can also be associated with diabetes, in particular type 2 diabetes. Hypertension is also evidenced in many patients in whom the causative agent or disorder is unknown. While such "essential" hypertension is often associated with disorders such as obesity, diabetes, and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure, and stroke (brain haemorrhaging). These conditions are associated with increased mortality. Hypertension can also contribute to the development of atherosclerosis and coronary disease. These conditions are also associated with increased mortality.

The exact cause of essential hypertension is unknown, though a number of factors are believed to contribute to the onset of the disease. Among such factors are stress, uncontrolled emotions, unregulated hormone release (e.g. dysfunctional renin-angiotensin-aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like has been developed and marketed as antihypertensives. The treatment of hypertension utilizing these compounds has proven beneficial in the prevention of death caused by e.g. heart failure, renal failure, and brain haemorrhaging. This implies that although high blood pressure is being reduced, the underlying cause of essential hypertension is not responding to this treatment.

Hypertension has been associated with elevated blood insulin levels, a condition known as hyperinsulinemia, and therefore appears to be linked to diabetes mellitus and prediabetic conditions e.g. obesity and the metabolic syndrome. Insulin, apart from promoting glucose utilization, acts also to promote protein synthesis and the formation and storage of neutral lipids. Additionally, insulin affects vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, a reduction of insulin levels in patients with hyperinsulinemia can prevent abnormal vascular growth and renal sodium retention caused by high insulin levels and thereby alleviates hypertension.

The term "hypertension" as used herein, relates to a state of abnormally increased blood pressure. Specifically, hypertension relates to a state in which blood pressure is consistently above 140/90 mmHg over a period of more than 1 month. Systolic blood pressure is the top number. Diastolic blood pressure is the bottom number. However in a specific embodiment of the present invention, hypertension relates to a state in which blood pressure is consistently above 130/80 mmHg or 120/80 mmHg or 110/70 mmHg. Hypertension may have no known cause (essential or idiopathic hypertension) or be associated with other primary diseases (secondary hypertension).

Hypertension as well as cardiovascular disorder risk factors can be estimated by measurement of blood pressure and heart rate levels measured by telemetry, visceral fat pads, circulating CVD risk factors: lipid profile, PAI1 etc., spontaneous physical activity and body temperature. The effects on left ventricular function of the heart can be measured by ultrasonical assessment of left ventricular function.

Hyperlipidemia is recognized as a primary risk factor in causing cardiovascular disease due to atherosclerosis, and is also associated with diabetes. The treatment and prevention of cardiovascular disease emphasize the need for reduction of plasma cholesterol levels, and low density lipoprotein cholesterol in particular. Other independent risk factors include glucose intolerance, left ventricular hypertrophy, hypertension, and being of the male sex. Cardiovascular disease is especially relevant among diabetic subjects, at least in part because of the existence of multiple independent risk factors in this population. Successful treatment of hyperlipidemia in the general population, and in diabetic subjects in particular, is therefore of tremendous medical importance.

The terms "dyslipidemia" or "hyperlipidemia" as used herein, relates to disorders or clinical conditions in the lipoprotein metabolism characterized by excess levels of blood lipids such as cholesterol and triglycerides, while HDL-cholesterol (high-density lipoprotein) is low. This condition is often associated with the occurrence of true diabetes and is often also accompanied by high blood pressure. A combination of these mentioned states are often referred to as "metabolic syndrome X" or "metabolic syndrome", as explained elsewhere herein.

The term "retinopathy" as used herein refers to a noninflammatory degenerative damage to the retina of the eye. Retinopathy frequently occurs secondary to diabetes, but may also result from hypertension.

The term "neuropathy" as used herein refers to any disease that affects any part of the nervous system. Thus, neuropathy relates to any problem in peripheral nerve function (any part of the nervous system except the brain and spinal cord) that causes pain, numbness, tingling, swelling, and muscle weakness in various parts of the body.

The terms "microangiopathy" and "macroangiopathy" as used herein, refers to any disease resulting from complication in the small blood vessels (eyes, kidneys, nerves), and large blood vessels (arteriosclerosis, cardiovascular disease), respectively.

The term "hypercholesterolemia" as used herein refers to the presence of high levels of total and LDL-cholesterol in the blood. Though not in itself a disease, hypercholesterolemia is secondary to many disorders and can contribute to many forms of disease, for example cardiovascular disease.

Specifically, hypercholesterolemia relates to blood cholesterol levels above 200 mg/mL (i.e. above 5.2 mmol/l) (ATPIII guidelines).

The term "hyperinsulinemia" as used herein refers to a condition in which the level of insulin in the blood is higher than normal. Hyperinsulinemia is caused by overproduction of insulin The term "a person in need thereof" as used herein, is meant to comprise human beings, who has or is at risk of developing at least one of the disorders and/or clinical conditions mentioned herein.

The term "genetic disposition" as used herein is meant to comprise any genetic variation, which increases the relative risk of developing a disorder or condition according to the present invention. A genetic disposition may be apparent from observations of a family history of the disorder or condition. The genetic variation may also be determined by biochemical and/or biological methods known to persons skilled within the art.

The term "obesity" as used herein relates to increased body weight caused by excessive accumulation of body fat. Obesity may for example be observed by assessing body mass index (BMI), defined as weight (W) in kg divided by squared height (H) in meters, i.e. (W (kg)/$H^2$ ($M^2$)). In Europe and USA, obesity is often defined by a BMI above 30, while BMI between 25 and 30 is defined as overweight. Other ethnic groups, such as Asian populations, are considered to be obese at lower BMI (World Health Organ Tech Rep Ser. 2000; 894: i-xii, 1-253). In the present invention, a human being is considered to be overweight or obese, when BMI is above 25, for example 26, such as 27, for example 28, such as 29, for example 30. In the context of the present invention, the term "obesity" preferably relates to visceral obesity Treatment It is within the scope of the present invention to provide methods, uses, compounds, compositions and kits-of parts for treating, preventing or ameliorating diabetes, in particular type 2 diabetes and/or a clinical condition associated with type 2 diabetes.

More specifically, a method is provided of treating, preventing or ameliorating type 2 diabetes and/or a clinical condition associated with type 2 diabetes, which method comprises administering an effective amount of cafestol or a derivative thereof to a person in need thereof.

Moreover, a cafestol compound or a derivative thereof is provided for use in the treatment of type 2 diabetes and/or a clinical condition associated with type 2 diabetes. Compositions comprising a cafestol compound or a derivative thereof are also provided for such use. Such compositions may be formulated as pharmaceutical compositions, but food supplements are also contemplated.

In addition, a method is provided for increasing insulin secretion and/or increasing insulin-dependent glucose uptake, said method comprising administering an efficient amount of cafestol to a person in need thereof.

The treatment, prevention and/or amelioration of diabetes, such as type 2 diabetes and/or an associated clinical condition may also involve an additional agent suitable for treating, preventing or ameliorating diabetes, such as type 2 diabetes and/or a clinical condition associated therewith.

As indicated, the provided methods, uses, compounds, compositions and kits-of parts relates to both treating, preventing and/or ameliorating type 2 diabetes and/or a clinical condition associated with type 2 diabetes. Thus, the methods, uses, compounds, compositions and kits-of parts may be applied in a person, which does not yet suffer from any of the disorders or conditions specified herein. In this case, the treatment is a prophylactic treatment aiming at reducing the risk of acquiring type 2 diabetes and/or a clinical condition associated with type 2 diabetes.

It is also an object of the present invention to provide use of cafestol or a derivative thereof for the manufacture of a medicament for the treating, preventing or ameliorating a diabetes or a clinical condition associated with diabetes, in particular type 2 diabetes.

Disorders

The methods, uses, compounds, compositions and kits-of parts provided herein are generally intended for treating, preventing or ameliorating diabetes, in particular type 2 diabetes and/or a clinical condition associated with diabetes, in particular type 2 diabetes.

Type 2 Diabetes

Diabetes mellitus is a metabolic disorder characterized by hyperglycemia (high blood sugar). Diabetes is currently classified into type 1 diabetes, type 2 diabetes, other specific types of diabetes as well as gestational diabetes mellitus (DIABETES CARE, VOLUME 36, SUPPLEMENT 1, JANUARY 2013). A common cause of diabetes is inability of beta cells of the pancreas to produce sufficient insulin to prevent hyperglycemia. Type 1 is usually due to autoimmune destruction of the pancreatic beta cells. The hallmark of type 2 is tissue-wide insulin resistance. Initially, the pancreatic beta cells will attempt to compensate for the insulin resistance by increased insulin production. As a result, due to the exhausting insulin producing activity, type 2 diabetes mellitus, sometimes progresses to loss of beta cell function as well. Gestational diabetes is similar to type 2 diabetes mellitus, in that it involves insulin resistance. In gestational diabetes, the hormones of pregnancy cause insulin resistance in those women genetically predisposed to developing this condition.

Clinical Conditions Associated with Type 2 Diabetes

Insulin resistance and type 2 diabetes is associated with a number of serious clinical conditions. The term "clinical condition" as used herein is meant to comprise any disorder, disease or pathological condition.

Thus, according to the present invention, cafestol and derivatives thereof can also be utilized in treating, preventing or ameliorating any clinical condition associated with insulin resistance. This also means that cafestol and derivatives thereof can be used in treating, preventing or ameliorating any clinical condition associated with diabetes, in particular any clinical condition associated with type 2 diabetes.

Conditions associated with insulin resistance and/or diabetes include atherosclerosis, arteriosclerosis, arteriolosclerosis, hypertension, cardiovascular disorders, type 2 diabetes mellitus, retinopathy, neuropathy, nephropathy, microangiopathy, macroangiopathy, hyperglycemia, hypercholesterolemia, hyperinsulinemia, hyperlipidemia, overweight, visceral obesity, dyslipidemia, insulin resistance, impaired oral glucose tolerance, impaired fasting glucose, metabolic syndrome, polycystic ovary syndrome, fatty liver (steatosis hepatis), ischemia, ischemic heart disease, thrombotic stroke, haemorrhagic stroke, limb ischemia, and/or claudication. Each of the disorders or conditions specified above is intended to be an individual embodiment.

Consequently, methods, uses, compounds, compositions and kits-of parts for treating, ameliorating, and/or preventing each of them according to the present invention may be claimed individually.

Thus, in one embodiment, the invention relates to methods, uses, compounds, compositions and kits-of parts for treating, ameliorating, and/or preventing a clinical condition selected from the group consisting of atherosclerosis, arteriosclerosis, arteriolosclerosis, hypertension, cardiovascular disorders, type 2 diabetes mellitus, retinopathy, neuropathy, nephropathy, microangiopathy, macroangiopathy, hyperglycemia, hypercholesterolemia, hyperinsulinemia, hyperlipidemia, overweight, visceral obesity, dyslipidemia, insulin resistance, impaired fasting glucose, metabolic syndrome, polycystic ovary syndrome, fatty liver (steatosis hepatis), ischemia, ischemic heart disease, thrombotic stroke, haemorrhagic stroke, limb ischemia, or claudication.

In a preferred embodiment, the methods, uses, compounds, compositions and kits-of parts relates to treating, preventing or ameliorating metabolic syndrome. Metabolic syndrome is a cluster of metabolic risk factors in an individual. These risk factors include overweight/obesity, hypertension/cardiovascular disorders, type 2 diabetes mellitus, and dyslipidemia. Thus, the term "metabolic syndrome" according to the present invention is meant to comprise those risk factors. Metabolic syndrome is also sometimes referred to as metabolic syndrome X, syndrome X, insulin resistance syndrome, Reaven's syndrome or CHAOS. As is apparent from above, the individual risk factors involved in metabolic syndrome may also constitute an individual clinical condition associated with type 2 diabetes, which may also be treated using the methods, uses, compounds, compositions and kits-of parts provided herein.

In a particular embodiment, the methods, uses, compounds, compositions and kits-of parts of the present invention can be used for treating, preventing or ameliorating a cardiovascular disorder selected from the group consisting of atherosclerosis, arteriosclerosis, arteriolosclerosis, hypertension, microangiopathy, macroangiopathy, metabolic syndrome, ischemia, ischemic heart disease, thrombotic stroke, haemorrhagic stroke, limb ischemia, and claudication.

In a particular embodiment, the methods, uses, compounds, compositions and kits-of parts of the present invention can be used for treating, preventing or ameliorating neuropathy.

In a particular embodiment, the methods, uses, compounds, compositions and kits-of parts of the present invention can be used for treating, preventing or ameliorating nephropathy.

In a particular embodiment, the methods, uses, compounds, compositions and kits-of parts of the present invention can be used for treating, preventing or ameliorating retinopathy.

In a particular embodiment, the methods, uses, compounds, compositions and kits-of parts of the present invention can be used for treating, preventing or ameliorating dyslipidemia. In a particular embodiment, the methods, uses, compounds, compositions and kits-of parts of the present invention can be used for treating, preventing or ameliorating a condition associated with dyslipidemia selected from the group consisting of hypercholesterolemia, hyperlipidemia, overweight/obesity, and visceral obesity.

In a particular embodiment, the methods, uses, compounds, compositions and kits-of parts of the present invention can be used for treating, preventing or ameliorating a disorder associated with type 2 diabetes selected from the group consisting of hyperglycemia, hyperinsulinemia, overweight/obesity, visceral obesity, insulin resistance, and impaired oral glucose tolerance.

In a particular embodiment, the methods, uses, compounds, compositions and kits-of parts of the present invention can be used for treating, preventing or ameliorating diabetes, hypertension and/or cardiovascular disorders.

In a particular embodiment, the methods, uses, compounds, compositions and kits-of parts of the present invention can be used for treating, preventing or ameliorating hypertension.

In a particular embodiment, the methods, uses, compounds, compositions and kits-of parts of the present invention can be used for treating, preventing or ameliorating cardiovascular disorders.

In another embodiment, the methods, uses, compounds, compositions and kits-of parts of the present invention can be used for treating, preventing or ameliorating diabetes, and especially type 2 diabetes, including treatment or prevention of long-term complications, such as retinopathy, neuropathy, nephropathy, and micro- and macroangiopathy; treatment of hyperglycemia, hypercholesterolemia, hypertension, hyperinsulinemia, hyperlipidemia, atherosclerosis or ischemia.

Active Agent

Cafestol serves to increase glucose-dependent insulin secretion. Moreover, cafestol increases glucose uptake in skeletal muscle cells. Thus, cafestol has the dual function of increasing insulin secretion in response to glucose and increasing insulin sensitivity. Therefore, cafestol and derivatives thereof are prominent therapeutic agents for treating, preventing or ameliorating diabetes. Thus, cafestol and derivatives thereof can be used according to the present invention for treating, preventing or ameliorating any type of diabetes, i.e. type I, type 2 and gestational diabetes. In particular, cafestol and derivatives thereof can be used according to the present invention for treating, preventing or ameliorating diabetes associated with insulin resistance, such as type 2 and gestational diabetes. However, in a most preferred embodiment, the methods, uses, compounds, compositions and kits-of parts of the invention are related to treating, preventing or ameliorating type 2 diabetes and/or clinical conditions or disorders associated with type 2 diabetes.

A range of methods, uses, compound& compositions and kits-of parts are provided herein, which involve cafestol and/or a derivative thereof. For example, a method is provided for treating, preventing or ameliorating diabetes, preferably type 2 diabetes, and/or a clinical condition associated with diabetes, preferably type 2 diabetes, which method comprises administering an effective amount of cafestol or a derivative thereof to a person in need thereof. Cafestol or a derivative thereof are also provided for use in treating, preventing or ameliorating diabetes, preferably type 2 diabetes, and/or a clinical condition associated with diabetes, preferably type 2 diabetes.

The methods, uses, compounds, compositions and kits-of parts provided herein may employ cafestol obtained from any source, such as isolated from coffee beans. However, in one specific embodiment, the cafestol and/or derivatives thereof are synthetically produced by chemical synthesis.

Cafestol and its ester is one of the main components of the diterpene ester fraction of coffee bean oil. Cafestol has the following chemical formula:

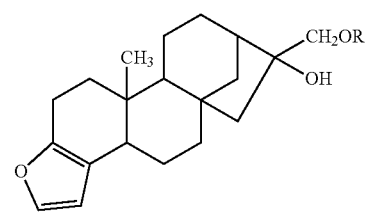

Cafestol

Another one of the principle components of the diterpene ester fraction of coffee bean oil is kahweol ester. Kahweol has the following formula:

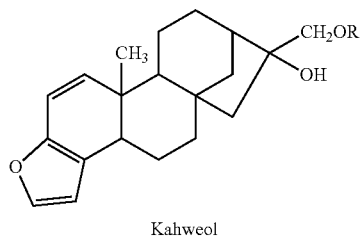

Kahweol

Cafestol and Kahweol are structurally very similar, and Kahweol is therefore in the present context understood as a derivative of cafestol according to the present invention. Thus, the methods, uses, compounds, compositions and kits-of parts in one embodiment involve the use of kahweol or derivatives thereof for treating, preventing or ameliorating diabetes, in particular type 2 diabetes.

The term "derivatives" as used herein is meant to include compounds, in which one atom or a group of atoms is replaced with another atom or a group of atoms. In addition, derivatives include isomers or mixtures of isomers as well as pharmaceutically acceptable salts, solvates, esters and prodrugs of cafestol or kahweol.

It is also understood that "derivatives" of cafestol and kahweol, also include any and all safe and effective derivatives, analogs, or precursors of cafestol and kahweol, in particular, their esters and salts. Salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmitate, pectinate, persulfate, 3-phenylpropionate, picrate, pivalate, propionate, succinate, tartrate, thiocyanate, tosylate, mesylate and undecanoate, and/or any mixtures thereof. In one embodiment, cafestol salts or kahweol salts are selected from the group consisting of acetate, diacetate, palmitate, linoleate, stearate, eicosanoate, myristate, docosanoate, and tetracosanoate; also cafestol toluenesulfonate; and 16, 17 anhydrocafestol, or any mixtures thereof. Many of these materials are naturally occurring components of coffee bean oil, albeit in small concentrations.

In preferred embodiments of the methods, uses, compounds, compositions and kits-of parts provided herein, cafestol and/or salts and esters thereof are employed.

Cafestol is available commercially in esterified form as cafestol acetate, and thus, specific embodiments of the methods, uses, compounds, compositions and kits-of parts of the present invention involve cafestol acetate. However, in another embodiment, the derivative is cafestol palmitate.

Other examples of derivatives can be found in Lam et al, J Med Chem. 1987 August; 30(8):1399-403 and in "Coffee" vol. 1-6 by R. J. Clarke.

The term "pharmaceutical acceptable salt, solvate or prodrug" as used herein refers to those acid and base additions salts, solvates, and prodrugs of the compounds of the present invention which are, within the scope of sound medical judgment, suitable for use without undue toxicity, irritation, allergic response, and the like, commensurate with a reasonable benefit/risk ratio, and effective for their intended use, as well as the zwitterionic forms, where possible, of the compounds of the invention.

Pharmaceutically acceptable acid and base addition salts refers to the relatively non-toxic, inorganic and organic salts of compounds of the present invention. These salts can be prepared in situ during the final isolation and purification of the compounds, or by subsequently reacting the purified compound in its free acid or base form with a suitable organic or inorganic compound and isolating the salt thus formed. In so far as the cafestol and kahweol are basic compounds, they are capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt.

The pharmaceutically acceptable acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Salts may be prepared from inorganic acids sulfate, pyrosulfate, bisulfate, sulfite, bisulfate, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts may also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts may include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. (See, for example, Berge S. M. et al., "Pharmaceutical Salts," *J. Pharm. Sci.*, 1977; 66:1-19 which is incorporated herein by reference.)

The cafestol and kahweol compounds of the present invention may exist in unsolvated forms as well as in solvated forms, including hydrated forms. In general, the solvated forms, including hydrated forms, are equivalent to unsolvated forms and are intended to be encompassed within the scope of the present invention.

The term "prodrug" refers to compounds that are rapidly transformed in vivo to yield the parent compound of the above formulae, for example, by hydrolysis. A thorough discussion is provided in T. Higuchi and V Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference. Examples of prodrugs include pharmaceutically acceptable, non-toxic esters of the compounds of the present invention, including $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. $C_1$-$C_4$ alkyl esters are preferred. Esters of the compounds of the present invention may be prepared according to conventional methods "March's Advanced Organic Chemistry, $5^{th}$ Edition". M. B. Smith & J. March, John Wiley & Sons, 2001.

Cafestol and kahweol compounds may contain chiral centers and therefore may exist in different enantiomeric and diastereomeric forms. This invention relates to all optical isomers and all stereoisomers of cafestol and kahweol compounds, both as racemic mixtures and as individual enantiomers and diastereoismers ((+)- and (−)-optically active forms), and mixtures thereof, and to all pharmaceutical compositions and methods of treatment defined elsewhere herein that contain or employ them, respectively. Individual isomers can be obtained by known methods, such as optical resolution, optically selective reaction, or chromatographic separation in the preparation of the final product or its intermediate.

The active component is preferably substantially pure, i.e., at least 70% pure, preferably at least 80% pure and more preferably at least 90% pure, such as at least 91%, such as at least 92%, such as at least 93%, such as at least 94%, such as at least 95%, such as at least 96%, such as at least 97%, such as at least 98%, such as at least 99%, such as at least 99.5% pure, Administration The compounds, compositions or kit-of-parts provided herein may be administered by any suitable method available in the art. The main routes of administration are parenteral injections, oral, and topical, as will be described below. Other drug-administration methods, such as subcutaneous injection, which are effective to deliver the drug to a target site or to introduce the drug into the bloodstream, are also contemplated. Furthermore, intranasal administration and administration by pulmonary inhalation is convenient and effective methods of administration, which could be used.

The compounds, compositions or kit-of-parts of the present invention are preferably administered orally, for example as an oral tablet or capsule or a liquid extract. This is a convenient non-invasive approach for administration, which is also preferred by most patients. The compounds, compositions and kit-of-parts are easily taken up via the gastrointestinal tract.

However, compounds, compositions or kits-of-parts of the invention may also be administered parenterally. This could particularly be relevant, where the compound, composition or kit-of-parts is administered in combination with an additional agent, which requires parenteral injection. Thus, in one embodiment of the present invention, the compounds, compositions or kits-of-parts provided herein are administered parenterally, that is by intravenous, intramuscular, subcutaneous, intranasal, intrarectal, intravaginal or intraperitoneal administration. The subcutaneous and intramuscular forms of parenteral administration are generally preferred. Appropriate dosage forms for such administration may be prepared by conventional techniques. The compounds, compositions and kits-of-parts may also be administered by inhalation that is by intranasal and oral inhalation administration. In a preferred embodiment, the compounds, compositions or kits-of-parts of the present invention are delivered by intravenous, subcutaneous, and/or intra-muscular administration.

The compounds, compositions and kits-of-parts according to the invention may be administered with at least one other compound. The compounds, compositions and kits-of-parts may be administered simultaneously, either as separate formulations or combined in a unit dosage form, or administered sequentially.

Dosages

The dosage requirements will vary with the particular composition employed, the route of administration and the particular individual being treated. Ideally, an individual to be treated by the present method will receive a pharmaceutically effective amount of the compound, composition or kit-of-parts in the maximum tolerated dose, generally no higher than that required before drug resistance develops.

The methods and uses of the present invention provide that cafestol or a derivative thereof is administered in an effective amount. By "effective amount" herein is meant a dose that produces the therapeutic effects for which it is administered. The exact dose will depend on the clinical condition or disorder to be treated, and can be ascertained by one skilled in the art using known techniques. For example, the compound, composition and kit-of-parts of the present invention can be administered to a person in an amount of from 1 μg/kg to about 100 mg/kg per day. In addition, as is known in the art, adjustments for age as well as the body weight, general health, sex, diet, time of administration, drug interaction, the route and form of administration, and the severity of the clinical condition (e.g. decreased kidney and liver function) may be necessary, and will be ascertainable with routine experimentation by those skilled in the art.

Cafestol or a derivative can be administered in dosage ranges of 5 μg to about 20 g per day. In one embodiment, suitable dosage ranges of cafestol or a derivative thereof are typically 1-500 mg daily, preferably 1-100 mg daily, 70-200 mg daily, 70-150 mg daily and most preferably 1-30 mg daily, 30-70 mg daily, 40-60 mg daily, 45-55 mg daily or about 50 mg daily. In another embodiment, the suitable dose of cafestol or a derivative thereof is 10 µg/kg bodyweight daily, preferably 20 µg/kg bodyweight, and most preferably 25 µg/kg bodyweight or 30 µg/kg bodyweight or 40 µg/kg bodyweight or 50 µg/kg bodyweight or 60 µg/kg bodyweight.

The cafestol compound including a derivative thereof as defined elsewhere herein is preferably administered at least once daily, and may therefore be administered once or twice daily. As mentioned elsewhere herein, the doses of cafestol compound are preferably administered orally and/or subcutaneously.

Human data on cafestol pharmacokinetics and metabolite formation have been provided in detail by De Roos et al. (1998). In this study, cafestol disposition was investigated in healthy ileostomy volunteers. From the recovery of cafestol metabolites in the ileostomy effluent, it was estimated that approximately 70% was absorbed from the gastrointestinal tract. As only approximately 1% of the dose was recovered in urine, it was concluded from that study that cafestol is subject to extensive metabolism in the human body.

However, the parent cafestol is also rapidly absorbed into the portal vein. Two minutes after dosing, the parent compound represented 50% of the total radioactivity present in portal blood. It is remarkable that cafestol absorption continued during the next 50 min, still representing 70% of the activity present in portal blood at 50 min after administration. The presence of a glucuronide in bile found to be easily deconjugated by a bacterial enzyme, together with the prolonged absorption of parent compound from the gastrointestinal tract suggests that cafestol undergoes enterohepatic cycling. It should be mentioned that the cafestol dose used in the oral studies, 1.5 mg/mouse, is rather high compared with the amount present in coffee. Depending on the brewing, coffee may contain up to 3.5 mg/cup of 100 ml (Ranheim and Halvorsen, 2005). However, the exact concentration depends on several factors, such as brewing, roasting, storage conditions, type of bean and mixture of beans.

Target Group

The present invention provides methods and uses, which involves administering an effective amount of cafestol or a derivative thereof to a person in need thereof.

Generally, "a person in need thereof" is a person, who suffers from diabetes and/or a clinical condition associated with diabetes or a person who is at risk of developing diabetes and/or a clinical condition associated with diabetes; in particular type 2 diabetes. Such person also includes persons with one or more pre-diabetic conditions, such as insulin resistance and/or impaired glucose tolerance. However, a person in need may also be a subject with type 1 diabetes.

A person in need thereof thus includes any person having any level of insulin resistance or showing symptoms of insulin resistance. I other words, the methods, uses, compounds, compositions and kits-of parts are applicable to any person with decreased insulin sensitivity.

Insulin-sensitivity can be measured by several methods e.g. hyperinsulinemic euglycemic clamp studies, homeostasis model assessment (HOMA) and oral glucose tolerance test (OGGT). Secondary parameters may also be used as indicators of insulin sensitivity, e.g. fasting levels of circulating metabolites (e.g. triglycerides, Free Fatty Acids (NEFA)), levels of inflammatory cytokines (e.g. TNFα, IL-1, IFNγ, GM-CSF, IL-8, IL-15, IL-16, IL-17, IL-18, TGFβ, IL-6, IL-1RA, sIL-1Ri, sTNF-R, IL-4, IL-10, IL, 11, IL 13, CRP) and levels of hormones and adipokines (e.g. adiponectin, leptin, ghrelin, GLP-1, NPY, PYY).

Impaired oral glucose tolerance (IGT) is a measure of the response to an oral glucose tolerance test. In this test, a fasting individual is subjected to an oral administration of glucose, and it is subsequently monitored how quickly the glucose is cleared from the blood. The test is indicative for diabetes and insulin resistance. In one embodiment, the term "impaired oral glucose tolerance" (IGT) as used herein include a condition in which venous plasma glucose levels 2 hours after oral administration of 75 gram glucose is above 140 mg/dL (7.8 mmol/l) and below 200 mg/dL (11.1 mmol/l) and/or where fasting venous plasma glucose concentration is between 100 mg/dL (5.6 mmol/l) and 125 mg/dL (6.9 mmol/l). In one embodiment, the person in need thereof is a person with gestational diabetes mellitus, which can be determined by a 75-g OGTT performed at gestational week 24-28 and one or more of the following: fasting plasma glucose at or above 92 mg/dl (5.1 mmol/l), 1 hour plasma glucose at or above 180 mg/dl (10.0 mmol/l) or 2 hour plasma glucose at or above 153 mg/dl (8.5 mmol/l). (Diabetes Care vol 36, suppl 1, January 2013).

The term "hyperglycemia" as used herein, relates to a state of abnormally high levels of glucose in the blood. Specifically, hyperglycemia relates to a state in which fasting blood glucose level is consistently at or above 126 mg/dL (7.0 mmol/l) and/or venous plasma glucose levels 2 hours after oral administration of 75 gram glucose is at or above 200 mg/dL (11.1 mmol/l).

Hyperglycemia is also defined as a haemoglobin A1c at or above 48 mmol/mol (6.5%) or a non-fasting random plasma glucose level at or above 200 mg/dl (11.1 mmol/l) in a person with classic symptoms (Diabetes Care vol 36, suppl 1, January 2013). Thus, in one embodiment, a person in need thereof has fasting blood glucose level is consistently at or above 126 mg/dL (7.0 mmol/l) and/or venous plasma glucose levels 2 hours after oral administration of 75 gram glucose is at or above 200 mg/dL (11.1 mmol/l) and/or a haemoglobin A1c at or above 48 mmol/mol (6.5%) and/or a non-fasting random plasma glucose level at or above 200 mg/dl (11.1 mmol/l).

As mentioned herein above, the methods, uses, compounds, compositions and kits-of parts of the present invention can be applied in treating, preventing or ameliorating clinical conditions associated with diabetes, in particular type 2 diabetes. In one embodiment, such an associated clinical condition can be selected from the group consisting of atherosclerosis, arteriosclerosis, arteriolosclerosis, hypertension, cardiovascular disorders, type 2 diabetes mellitus, retinopathy, neuropathy, nephropathy, microangiopathy, macroangiopathy, hyperglycemia, hypercholesterolemia, hyperinsulinemia, hyperlipidemia, overweight, visceral obesity, dyslipidemia, insulin resistance, impaired oral glucose tolerance, impaired fasting glucose, metabolic syndrome, polycystic ovary syndrome, fatty liver (steatosis hepatis), ischemia, ischemic heart disease, thrombotic stroke, haemorrhagic stroke, limb ischemia, and claudication. Thus, it follows that "a person in need thereof" also include any person having or being at risk of acquiring a clinical condition can be selected from the group consisting of atherosclerosis, arteriosclerosis, arteriolosclerosis, hypertension, cardiovascular disorders, type 2 diabetes mellitus, retinopathy, neuropathy, nephropathy, microangiopathy, macroangiopathy, hyperglycemia, hypercholesterolemia, hyperinsulinemia, hyperlipidemia, overweight, visceral obesity, dyslipidemia, insulin resistance, impaired oral glucose tolerance, impaired fasting glucose, metabolic syndrome, polycystic ovary syndrome, fatty liver (steatosis hepatis), ischemia, ischemic heart disease, thrombotic stroke, haemorrhagic stroke, limb ischemia, and claudication.

Since the methods, uses, compounds, compositions and kits-of parts provided herein also encompass prophylactic treatment of diabetes, particularly type 2 diabetes, and associated clinical conditions, a person in need thereof also include any person, who does not yet suffer from any of the disorders or conditions specified herein, where a method of the invention comprise administering an effective amount of cafestol or a derivative thereof to said person in need thereof in order to prevent diabetes, such as type 2 diabetes and/or associated clinical conditions.

A person in need thereof also includes any person with a genetic disposition for diabetes, in particular type 2 diabetes. A genetic disposition can be verified by detection of genetic markers associated with or indicative of diabetes, in particular type 2 diabetes, or a clinical condition associated therewith. However, genetic disposition may also be determined on the basis of a family history of diabetes or associated clinical conditions.

Formulation

In one aspect, a cafestol compound or a derivative thereof is provided for use in treating, preventing or ameliorating type 2 diabetes and/or a clinical condition associated with diabetes, in particular type 2 diabetes. However, this treatment may also be combined with other agents, and thus, one aspect of the present invention relates to a cafestol compound or derivative thereof and at least one additional agent suitable for treating, preventing or ameliorating diabetes and/or a clinical condition associated with diabetes, for use in treating, preventing or ameliorating diabetes, in particular type 2 diabetes, and/or a clinical condition associated with diabetes, in particular type 2 diabetes.

The cafestol compound or derivative thereof and the at least one additional agent may be formulated as a pharmaceutical composition. Thus, a pharmaceutical composition is also provided comprising cafestol or a derivative thereof for use in treating, preventing or ameliorating diabetes and/or a clinical condition associated with diabetes, in particular type 2 diabetes.

However, the cafestol compound or derivative thereof and/or additional agent may also be formulated as a food supplement.

For administration, the cafestol compounds and derivatives thereof as defined herein above are ordinarily combined with one or more adjuvants appropriate for the indicated route of administration.

The pharmaceutical formulation may comprise up to 100 wt % cafestol or derivative thereof. Preferably, the pharmaceutical formulation comprises at least 50 wt %, such as at least 60, 70, 80 or 90 wt % cafestol or derivative thereof. In a preferred embodiment, the pharmaceutical formulation comprises in the range of 50 wt % to 95 wt %, such as 60-90, 60-80, 70-95, or 80-95 wt % cafestol or derivative thereof.

The remaining part of the pharmaceutical composition generally consists of or comprises suitable carriers, additives and/or adjuvants, for example a calcium-based carrier.

The pharmaceutical composition according to the present invention may comprise the lipophilic anthracycline in an amount of at least 0.1%, preferably at least 0.5%, more preferably at least 1% of said lipophilic anthracycline (w/w %).

Preferably the pharmaceutical composition according to the present invention may comprise the lipophilic anthracycline in an amount of 0.1 to 10 w/w %, such as e.g., from 0.1 to 8 w/w %, from 0.1 to 5 w/w %, from 1 to 5 w/w %, from 0.1 to 2.5 w/w %, from 0.1 to 1.5 w/w %, from 0.25 to 1.25 w/w %, from 0.5 to 2.5 w/w %, from 0.5 to 2.0 w/w %, from 0.5 to 1.5 w/w %, or of about 1.0 w/w %. More preferably in an amount of from 0.25 to 1.25 w/w %, and more preferably in an amount of 1.0 w/w %.

The cafestol compounds and derivatives thereof may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the cafestol compounds and derivatives thereof may be dissolved in saline, water, polyethylene glycol, propylene glycol, ethanol, corn oil, peanut oil, cottonseed oil, sesame oil, tragacanth gum, benzyl alcohol, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form including granules, powders or suppositories or in a liquid form such as solutions, suspensions, or emulsions. The pharmaceutical compositions may be subjected to conventional pharmaceutical operations such as sterilization and/or may contain conventional adjuvants, such as preservatives, stabilizers, wetting agents, emulsifiers, buffers, etc.

In a preferred embodiment, the cafestol compounds and derivatives thereof are formulated as a liquid or solid pharmaceutical composition suitable for oral administration. Solid dosage forms for oral administration may include capsules, tablets, pills, powders, and granules.

In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water.

Such compositions may also comprise adjuvants, such as wetting agents, emulsifying and suspending agents, and sweetening, flavoring, and perfuming agents.

The cafestol compounds and derivatives thereof of the present invention can be used for treating, preventing or ameliorating the diseases as disclosed herein in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogencontaining groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Other examples include salts with alkali metals or alkaline earth metals, such as sodium, potassium, calcium or magnesium or with organic bases.

While the cafestol compounds and derivatives thereof can be administered as the sole active pharmaceutical agent, they can also be used in combination with one or more additional agents. When administered as a combination, the therapeutic agents can be formulated as separate compositions which are given at the same time or different times, or the therapeutic agents can be given as a single composition.

For example, the compounds according to the present invention may be administered before, during or after the administration of the cafestol compound or derivative thereof, provided that the time between the administration of said compounds and the administration of the cafestol compound or derivative is such that ingredients are allowed to act synergistically. When simultaneous administration of the additional agents and a cafestol compound or derivative is envisaged, a composition containing both a cafestol compound or derivative and the additional agent may be particularly convenient. Alternatively, the additional agents according to the present invention and the cafestol compound or derivative may be administered separately in the form of suitable compositions.

To prepare the pharmaceutical compositions of this invention, an appropriate amount of the active ingredient(s), in salt form or base form, is combined in an intimate admixture with a pharmaceutically acceptable carrier, which can take a wide variety of forms depending on the form of preparation desired for administration. These pharmaceutical compositions are desirably in unitary dosage form suitable for administration orally, rectally, percutaneously, parenterally or by pulmonary inhalation or intranasal administration. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed.

It is especially advantageous to formulate the aforementioned pharmaceutical compositions in dosage unit form for ease of administration and uniformity of dosage. As used in the specification and claims, unit dosage form refers to physically discrete units suitable as unitary dosages, each unit containing a predetermined quantity of active ingredient(s) calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. For example, in one embodiment, formulations containing about one (1) milligram of active ingredient or, more broadly, about 0.01 to about ten (10) grams, per tablet, are suitable unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e. g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e. g., olive oil), and injectable organic esters (e. g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e. g., sterile, pyrogen-free water.

The compounds of the present invention may be formulated for topical administration to the epidermis as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, pre-determined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve.

Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP).

The powder carrier can for example form a gel in the nasal cavity. The powder composition may be presented in unit dose form for example in capsules or cartridges of e. g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e. g., Azone (1-dodecylazacycloheptan-2-one). Sustained release delivery systems are inserted subcutaneously into the subdermal layer by surgery or injection. The subdermal implants encapsulate the compound in a lipid soluble membrane, e. g., silicone rubber, or a biodegradable polymer, e. g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa.

Combination Treatment

The methods, uses, compounds, compositions and kits-of parts encompass treating, preventing or ameliorating diabetes, in particular type 2, and associated clinical conditions with an effective amount of cafestol or a derivative thereof and at least one additional agent. Thus, the cafestol compounds or derivatives thereof may also be beneficially combined with other active agents, which are used for treating, preventing or ameliorating diabetes, in particular type 2 and/or associated clinical.

Both diabetes types I and II are incurable chronic conditions. They are usually managed with a combination of dietary treatment and insulin supplementation. Careful control is needed to reduce the risk of long term complications. For type 2 diabetes, the primary focus is typically combinations of diet, exercise and weight loss, various oral diabetic drugs, and insulin use for patients not responding to oral medication. Oral diabetic drugs help control blood glucose levels in people who still produce some insulin, which is the majority of people with type 2 diabetes. These drugs are not insulin and are usually prescribed to people with diabetes along with recommendations for making specific dietary changes and getting regular exercise. The drugs may lower blood glucose by stimulating the pancreas to release more insulin, or improve insulin's ability to move glucose into cells especially into the muscle cells. The oral diabetic drugs are often used in combination to achieve optimal blood glucose control. Adequate treatment of diabetes, as well as increased emphasis on blood pressure and cholesterol control as well as lifestyle factors, such as smoking cessation, exercise and keeping a healthy body weight, seems to improve the risk profile of the complications related to diabetes.

So in one embodiment, a method is provided for treating, preventing or ameliorating diabetes, such as type 2, and/or a clinical condition associated with diabetes, which method comprises administering an effective amount of cafestol or a derivative thereof and at least one additional agent to a person in need thereof.

Thus, it is envisaged that the cafestol compounds and/or derivatives thereof as defined herein may be used in combination with at least one additional agent. By administration "in combination" is meant herein that said additional therapeutic agent may be administered prior to and/or during (including in a co-formulation) and/or after treatment with the cafestol compounds of the present invention. In one preferred embodiment, the cafestol compounds and derivatives thereof mentioned herein are administered together with one or more additional compounds in a "kit-of-parts" system, for simultaneous, sequential or separate administration.

In a preferred embodiment, the additional agent is an agent suitable for treating, preventing or ameliorating diabetes, in particular type 2 diabetes and/or an associated clinical condition. Examples of such additional agents, which are suitable for treatment of type 2 diabetes include:

Biguanides (metformin is generally accepted as the first-line agent in treatment of type 2 diabetes),
    sulfonylureas,
    meglitinides (glinides)
    acarbose
    bile acid sequestrants,
    dopamine-2-agonists,
    amylin mimetics,
    thiazolidinediones (glitazones),
    glucagon-like peptide-1 receptor agonists,
    dipeptidyl peptidase 4 inhibitors (DPP4 inhibitors)
    Sodium-glucose co-transporter 2 (SGLT2) inhibitors
    GPR40 agonists
    glucagon antagonists
    bromocriptine mesylate
    insulins Thus, the present invention provides methods, uses, compounds, compositions and kits-of parts encompass treating, preventing or ameliorating diabetes, in particular type 2, and associated clinical conditions with an effective amount of cafestol or a derivative thereof and at least one additional agent, wherein said additional agent is selected from a member of the group consisting of biguanides (metformin), sulfonylureas, meglitinides (glinides), acarbose, bile acid sequestrants, dopamine-2-agonists, amylin mimetics, thiazolidinediones (glitazones), glucagon-like peptide-1 receptor agonists, dipeptidyl peptidase 4 inhibitors (DPP4 inhibitors), sodium-glucose co-transporter 2 (SGLT2) inhibitors, G protein-coupled receptor agonists (e.g. GPR40 agonists), glucagon receptor antagonists, bromocriptine mesylate and insulins.

Kit-of-Parts

The present invention in one aspect provides a pharmaceutical composition comprising a cafestol compound or a derivative thereof and at least one additional active agent. The additional agent is preferably an agent suitable for treating, preventing or ameliorating diabetes, such as type 2, and/or a clinical condition associated with diabetes, such as type 2.

A kit-of-parts is also contemplated, which comprises cafestol or a derivative thereof and an additional agent suitable for treating, preventing or ameliorating diabetes and/or a clinical condition associated with diabetes.

Examples of suitable active agents are provided elsewhere herein.

The term "kit of parts" as used herein designates a combined preparation containing, as active substance, a cafestol compound or a derivative thereof and an additional agent suitable for the treatment of diabetes, preferably type 2 diabetes, for the simultaneous, separate or sequential administration, for treating, preventing or ameliorating diabetes and/or a clinical condition associated with diabetes, preferably type 2 diabetes. Preferably cafestol compound or a derivative thereof and an additional agent are associated to form a single active unit before administration to a person in need thereof. Examples of relevant additional agents are mentioned herein above.

The two individual components of the kit-of-parts form a functional unit, i.e. a functional true combination through a purpose-directed application. Due to their use in the kit-of-parts of the invention, the two active ingredients (cafestol compound or a derivative thereof and an additional agent) show a joint effect.

EXAMPLES

The effect of cafestol on insulin secretion and glucose-uptake

Example 1

Acute Effects of Cafestol on Insulin Secretion Form INS-1E Cells.

INS-1E cells were seeded onto 24 well plates before incubation experiments. At the day of the experiment the buffer was changed to a modified Krebs-Ringer-buffer and the cells were preincubated in the same buffer for 60 min. Hereafter the cells were incubated in the same buffer at low (3.3 mM) and high (16.7 mM) glucose supplemented with cafestol ($10^{-12}$ to $10^{-8}$ M) for 60 min whereafter the incubation buffer was removed for analysis of rat insulin.

The insulin secretion is shown in FIG. 1 (cafestol). A significant increase in insulin secretion was found for cafestol at high glucose at concentrations ranging from $10^{-10}$ M to $10^{-6}$ M (table 1).

TABLE 1

Acute insulin secretion studies (INS-1E)

| Glucose | Cafestol | Mean | Std. Error | Lower | Upper | p value |
|---|---|---|---|---|---|---|
| 3.3 mM | — | 0.2745 | 0.0232 | 0.2278 | 0.3212 | |
| 16.7 mM | — | 0.7786 | 0.02151 | 0.7354 | 0.8219 | |
| 16.7 mM | $10^{-12}$M | 0.8261 | 0.02967 | 0.7661 | 0.886 | 0.1926 |
| 16.7 mM | $10^{-10}$M | 0.8715 | 0.03385 | 0.8032 | 0.9399 | 0.0202 |
| 16.7 mM | $10^{-8}$M | 0.8682 | 0.0359 | 0.7956 | 0.9407 | 0.0304 |
| 16.7 mM | $10^{-6}$M | 0.9013 | 0.02951 | 0.8417 | 0.9609 | 0.001 |

Example 2

Chronic Effects of Cafestol on Insulin Secretion Form INS-1E Cells

INS-1E cells were seeded onto 24 well plates and incubated for 72 hours in RPMI 1640 supplemented with cafestol. After 72 hours the buffer was changed to a modified Krebs Ringer buffer and the cells were incubated for 60 min at low (3.3 mM) and high (16.7 mM) glucose. Hereafter the medium was removed for later insulin analysis using a sensitive rat insulin kit from Linco.

Long-term (72 hours) incubation with cafestol at $10^{-10}$ and $10^{-8}$ M resulted in a significant increase in glucose-(16.7 mM)-stimulated insulin secretion from the INS-1E cells. At low (3.3 mM) glucose cafestol at $10^{-12}$ significantly decreased insulin secretion, had a neutral effect at $10^{-10}$ M and a stimulatory effect at $10^{-8}$ M (FIG. 2, table 2),

TABLE 2

Chronic insulin secretion studies (INS-1E)

| Glucose | Cafestol | Mean | Std. Error | Lower | Upper | p value |
|---|---|---|---|---|---|---|
| 3.3 mM | — | 0.5893 | 0.01545 | 0.5579 | 0.6206 | |
| 3.3 mM | $10^{-12}$M | 0.4999 | 0.02334 | 0.4507 | 0.5492 | 0.002 |
| 3.3 mM | $10^{-10}$M | 0.5853 | 0.02433 | 0.534 | 0.6366 | 0.8869 |
| 3.3 mM | $10^{-8M}$ | 0.7482 | 0.02321 | 0.6993 | 0.7972 | <0.0001 |
| 16.7 mM | — | 0.9884 | 0.04041 | 0.9062 | 1.071 | |
| 16.7 mM | $10^{-12}$M | 0.9279 | 0.04994 | 0.8226 | 1.033 | 0.367 |
| 16.7 mM | $10^{-10}$M | 1.322 | 0.1007 | 1.109 | 1.534 | 0.0006 |
| 16.7 mM | $10^{-8}$M | 1.661 | 0.081 | 1.49 | 1.832 | <0.0001 |

Example 3

Acute Effects of Cafestol on Glucose-Uptake in Human Skeletal Muscle Cell Line

Human skeletal muscle cells were seeded in 24 wells, (0.3-$10^6$ cells/well) containing 1 mL growth medium (Promocell, Heidelberg, Germany). Once 70-90% confluence was reached, the growth medium was replaced by 1 mL differentiation medium (Promocell, Heidelberg, Germany). This medium was changed every 2nd day for two weeks until multinucleated syncytia was visible in microscope. Cells were washed twice with PBS. 300 µL of an alternatively modified-Krebs Ringer Buffer (containing 0.1% BSA with 0.1 mM glucose, 1.5 µCi deoxy-d-glucose 2-[1,2-3H (M)] (Perkin Elmer, 2740 Skovlunde, Denmark) and 100 nM insulin was put in each well. Five types of solutions were prepared: one with either cafestol or rosiglitazone (control), a second with a $10^{-6}$ M cafestol, a third with a $10^{-10}$ M cafestol, a fourth with a $10^{-12}$ M cafestol, and a fifth with a 10-8 M rosiglitazone. Cells were kept on ice while adding medium. After 15 minutes of incubation at 37° C., 5.0% CO2, cells were washed twice with the modified-Krebs Ringer Buffer supplemented with 0.1% BSA and 50 mM glucose, stopping the incubation and glucose uptake. Hereafter, 0.2 mL 0.1 M NaOH was added to each well for a 30 minute room temperature incubation. 0.1 mL was transferred from each well to a 24 well counting plate (Wallac Oy, Turku, Finland). After adding 0.9 mL Hisafe II scintillator (Perkin Elmer, 2740 Skovlunde, Denmark), plates were stored in the dark for 12 hours before counted using a Trilux Micro Beta Counter (Wallac Oy, Turku, Finland). "Counts per minute" is a direct measure of glucose uptake.

Figure 3:
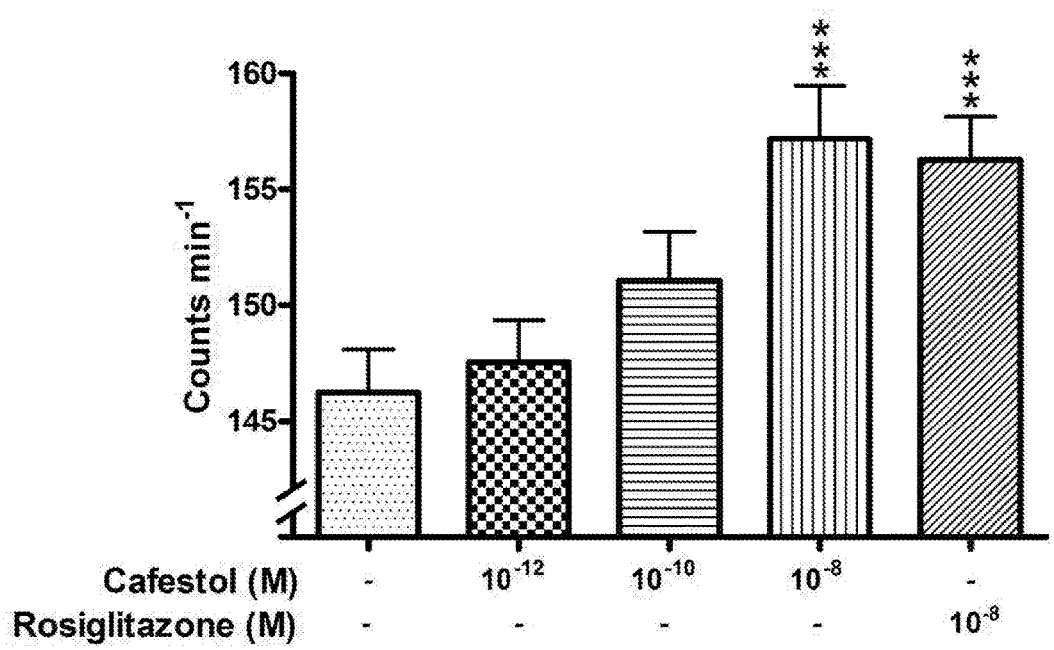
FIG. 3. Effect of cafestol on glucose-uptake in human skeletal muscle cell line.

The glucose-uptake was significantly increased at a cafestol concentration of $10^{-8}$ M (FIG. 3, table 3). Rosiglitazone ($10^{-10}$ M) was used as a positive control.

TABLE 3

Human skeletal muscle cell glucose uptake studies

| Group | Counts per minute (± in SEM) | p value |
|---|---|---|
| Negative control | 146.3 ± 1.839 | |
| $10^{-12}$ M Cafestol | 146.3 ± 1.839 | 0.6200 |
| $10^{-10}$ M Cafestol | 151.0 ± 2.104 | 0.0931 |
| $10^{-8}$ M Cafestol | 157.2 ± 2.318 | 0.0006 |
| Rosiglitazone | 156.3 ± 1.888 | 0.0004 |

Example 4

Effects of Cafestol on in Diabetic KKAY Mice

The effects of cafestol were investigated in a 10 week dietary intervention study in a type 2 diabetic animal model. Five weeks old male KKAy mice were randomly assigned to either of three intervention groups (n=12 per group), i.e. 1) Control (no cafestol added), 2) supplementation with 0.382 mg/day of cafestol/kg mice, and 3) supplementation with 1.146 mg/day of cafestol/kg mice. The cafestol was added to food pellets daily. At the beginning of the study (week 0) fasting blood glucose, insulin and lipids (total cholesterol, LDL, HDL and triglycerides) were measured. Every $2^{nd}$ week fasting blood glucose, body weight and food intake was measured. At the end of the intervention (week 10) fasting blood glucose, insulin, glucagon and lipids (total cholesterol, LDL-cholesterol, HDL-cholesterol) were measured. The pancreas was removed and treated with collagenase and subsequently, the effects on insulin secretory capacity was studied in isolated islets of Langerhans. Furthermore, gene expression levels of key regulatory genes in liver, fat and muscle tissues were measured using RT-PCR.

Figure 4:
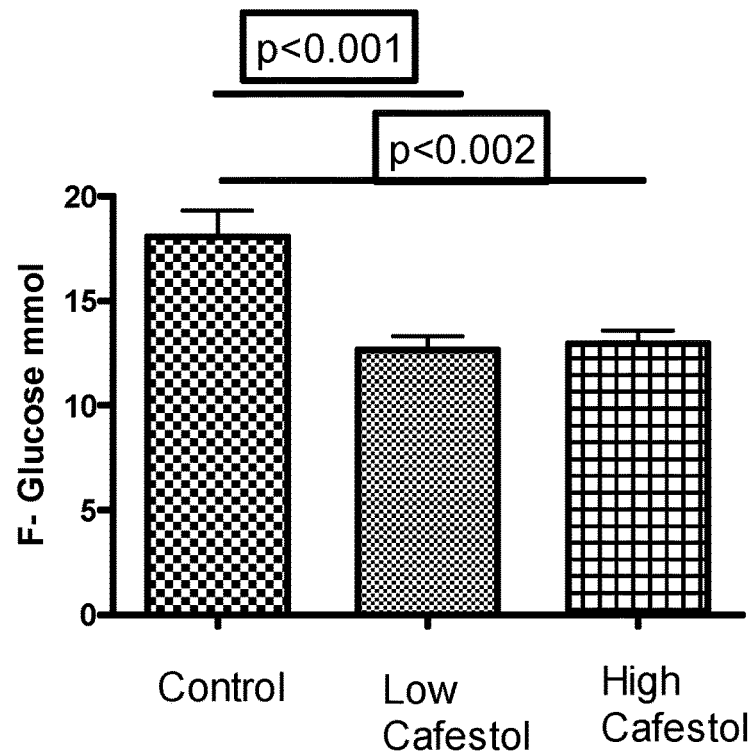
FIG. 4. Fasting plasma glucose after 10 weeks intervention.

As can be seen in FIG. 4, fasting plasma glucose is significantly decreased in the cafestol groups both at low concentration=0.382 mg/day/kg and the high concentration=1.146 mg/day/kg compared to the control group.

Figure 5:
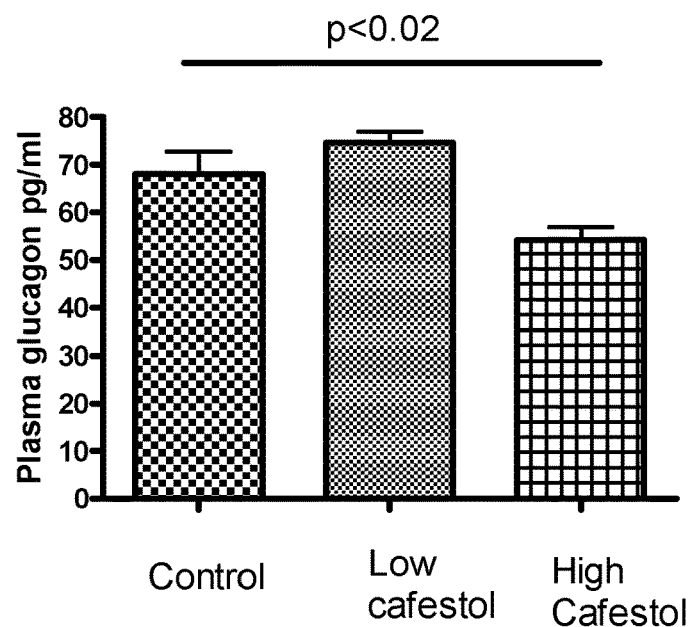
FIG. 5. Fasting plasma glucagon after 10 weeks intervention

FIG. 5 shows that the plasma glucagon is significant decreased in the High cafestol group (1.146 mg/day/kg) compared to Control. A suppression of glucagon may improve the glucose metabolism in type 2 diabetes. The suppression of circulating glucagon concentration reduces blood glucose levels due to an inhibition of the conversion of stored liver glycogen into glucose being released into the bloodstream.

Figure 6:
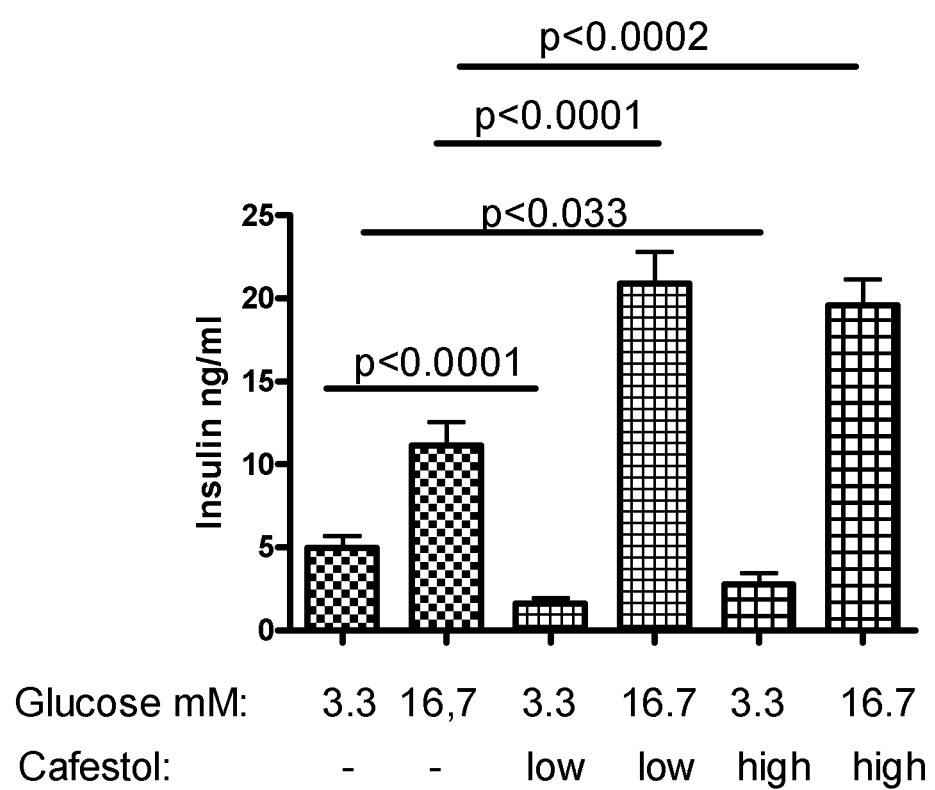
FIG. 6. Secretion experiment with langerhanske islets from KKAy mice after 10 weeks intervention.
Figure 7:
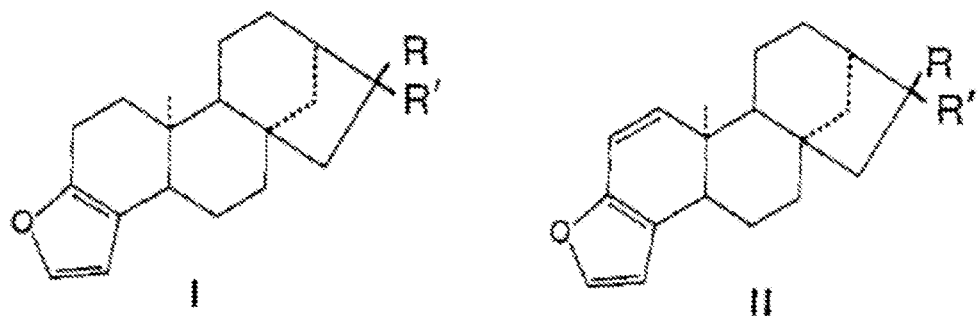
FIG. 7. Examples of cafestol and kahweol derivatives; cf. Lam et al, J Med Chem. 1987 August; 30(8):1399-403
Figure 7:
Figure 7:
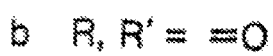
Figure 7:
Figure 7:
Figure 7:
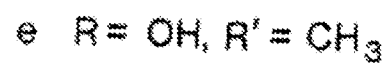
Figure 7:
Figure 7:
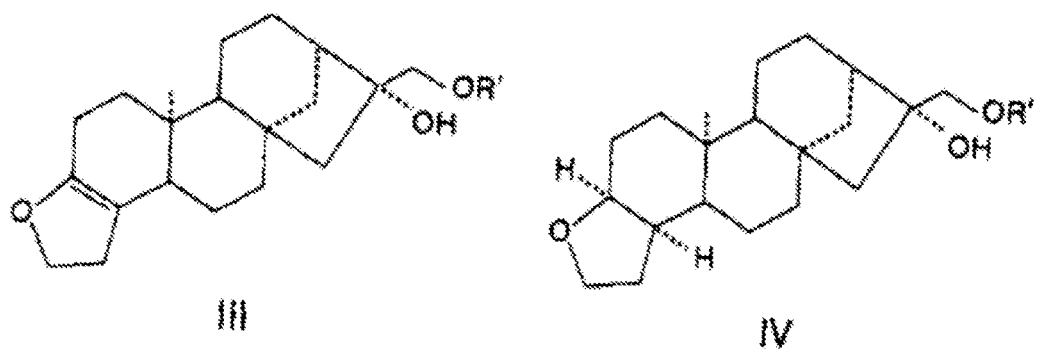
Figure 7:
Figure 7:
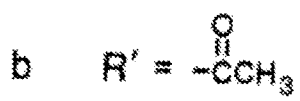

FIG. 6 demonstrates that the islets have become more glucose sensitive after the 10 weeks intervention with cafestol when compared to Control.

Figure 2:
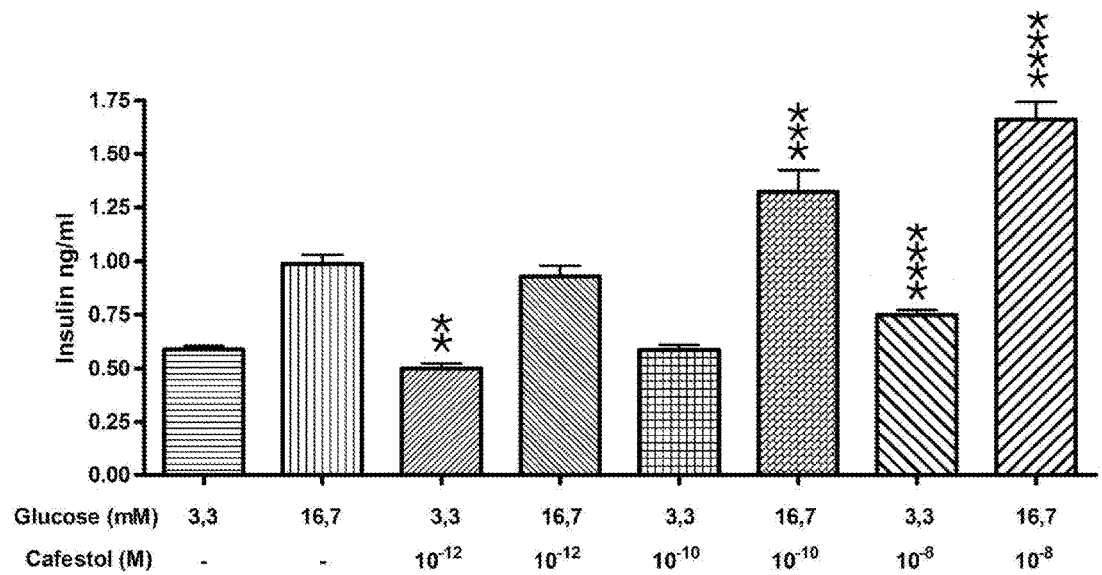
FIG. 2. Effect of long-term (72 hours) incubation with cafestol on glucose-(16.7 mM)-stimulated insulin secretion from INS-1E cells.

Furthermore, a significant glucagonostatic effect is seen at the low glucose level when treated with cafestol, which in diabetes terms are beneficial for counteract hypoglycemia (FIG. 2).

Figure 8:
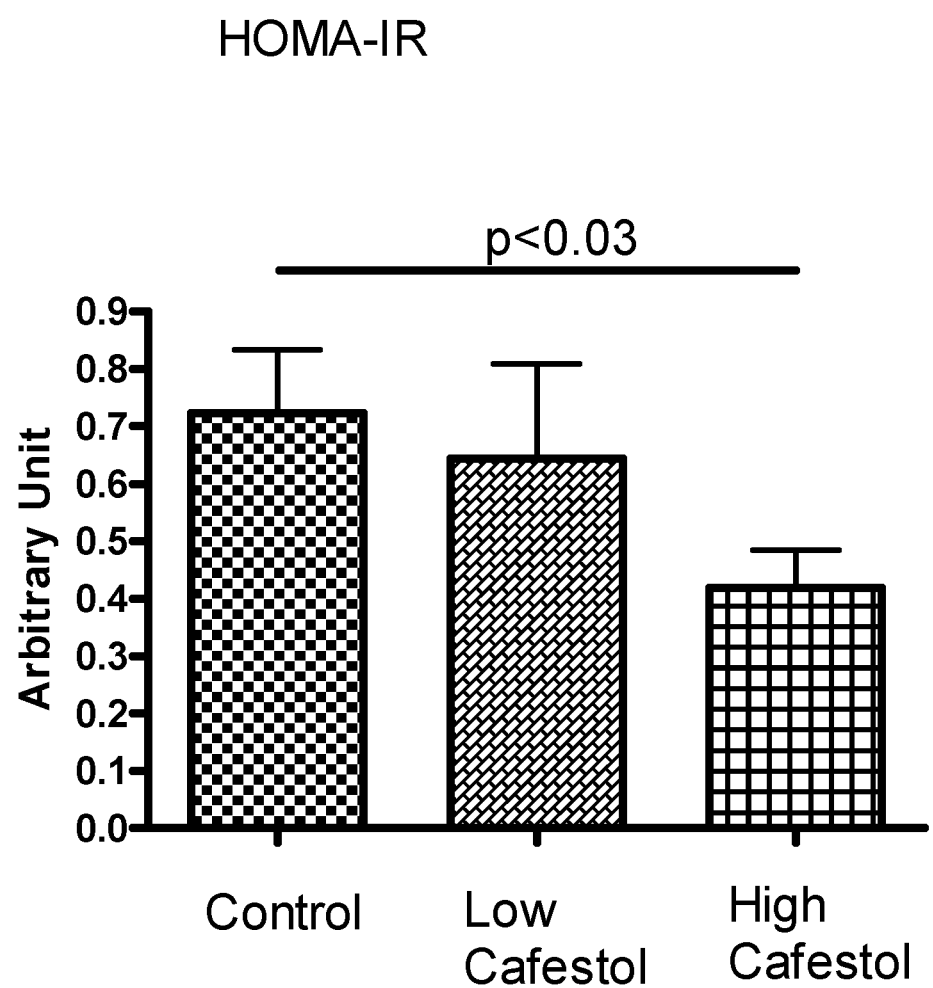
FIG. 8. HOMA—IR calculation demonstrating changes in insulin sensitivity based on fasting insulin and glucose data.

FIG. 8 illustrates the development of insulin response in a homeostasis model assessment (HOMA-IR). Following 10 weeks of intervention with cafestol in diabetic KKAY mice, the HOMA-IR was significantly reduced p=0.03 for the high dose of cafestol compared to control group. The low dose also showed a tendency to be reduced. Thus, it is seen that insulin sensitivity is increased after 10 weeks treatment with cafestol.

Conclusion

The above examples illustrate that cafestol is able to decrease fasting plasma glucose significantly for both low and high doses of cafestol. Cafestol seems to decrease the plasma concentration of the diabetogenic hormone, glucagon, which often is increased in diabetic subjects and lead to increased blood glucose level.

The beta cells in the Langerhanske Islets have become more glucose sensitive after 10 weeks intervention with cafestol, as the response is higher in the group treated with cafestol compared with control. Interestingly, the insulin stimulation is not present at low glucose concentration, which minimize the risk for hypoglycemia when cafestol is present, which indicate that cafestol is glucose dependent. The HOMA-IR is increased when the diabetic KKAY mice has been treated in 10 week with cafestol. The high dose of cafestol was associated with a significant decrease in HOMA-IR and thereby demonstrate an increase insulin sensitivity in liver, muscles and fat tissue.

The invention claimed is:

1. A method of treating, preventing or ameliorating insulin resistance, which method comprises administering a pharmaceutical formulation comprising isolated and purified cafestol, kahweol or pharmaceutically acceptable salts, solvates, esters or prodrugs thereof, wherein said isolated and purified cafestol, kahweol or pharmaceutically acceptable salts, solvates, esters or prodrugs thereof is at least 70% pure, and wherein said isolated and purified cafestol, kahweol or pharmaceutically acceptable salts, solvates, esters or prodrugs thereof is administered in a dosage of 30-500 mg daily to a person in need thereof.

2. The method according to claim 1, wherein said person in need thereof is a person having impaired oral glucose tolerance (IGT) and/or hyperglycemia.

3. The method according to claim 2, wherein said person in need thereof is a person having a fasting blood glucose level above 126 mg/dL (7.0 mmol/l) and/or venous plasma glucose levels 2 hours after oral administration of 75 gram glucose at or above 200 mg/dL (11.1 mmol/l), and/or said person in need thereof is at gestational week 24-28 and has a fasting plasma glucose at or above 92 mg/dl (5.1 mmol/l), 1 hour after oral administration of 75 gram glucose has a plasma glucose at or above 180 mg/dl (10.0 mmol/l) or 2 hours after oral administration of 75 gram glucose has a plasma glucose at or above 153 mg/dl.

4. The method according to claim 1, wherein said isolated and purified cafestol, kahweol or pharmaceutically acceptable salts, solvates, esters or prodrugs thereof is administered by oral administration.

5. The method according to claim 1, wherein an additional agent suitable for treating, preventing or ameliorating insulin resistance is administered to said person in need thereof.

6. The method according to claim 5, wherein said additional agent is selected from a member of the group consisting of biguanides, sulfonylureas, meglitinides, acarbose, bile acid sequestrants, dopamine-2-agonists, amylin mimetics, thiazolidinediones, glucagon-like peptide-1 receptor agonists, dipeptidyl peptidase 4 inhibitors, sodium-glucose co-transporter 2 inhibitors, G protein-coupled receptor agonists, glucagon receptor antagonists, bromocriptine mesylate and insulin.

7. The method according to claim 1, wherein said person in need thereof has type 2 diabetes and/or has a clinical condition associated with type 2 diabetes.

8. The method according to claim 7, wherein said clinical condition associated with type 2 diabetes is selected from the group consisting of atherosclerosis, arteriosclerosis, arteriolosclerosis, hypertension, cardiovascular disorders, type 2 diabetes mellitus, retinopathy, neuropathy, nephropathy, microangiopathy, macroangiopathy, hyperglycemia, hypercholesterolemia, hyperinsulinemia, hyperlipidemia, overweight, visceral obesity, dyslipidemia, insulin resistance, impaired oral glucose tolerance, impaired fasting glucose, metabolic syndrome, polycystic ovary syndrome, fatty liver (steatosis hepatis), ischemia, ischemic heart disease, thrombotic stroke, haemorrhagic stroke, limb ischemia, and/or claudication.

9. A method of increasing insulin secretion and/or increasing insulin dependent glucose uptake, said method comprising administering an effective amount of isolated and purified cafestol, kahweol or pharmaceutically acceptable salts, solvates, esters or prodrugs thereof to a person in need thereof, wherein said isolated and purified cafestol, kahweol or pharmaceutically acceptable salts, solvates, esters or prodrugs thereof is at least 70% pure, and wherein said isolated and purified cafestol, kahweol or pharmaceutically acceptable salts, solvates, esters or prodrugs thereof is administered in a dosage of 30-500 mg daily.

* * * * *